US00PP19454P2

(12) United States Plant Patent
Danziger

(10) Patent No.: US PP19,454 P2
(45) Date of Patent: Nov. 18, 2008

(54) ***VERBENA* PLANT NAMED 'DANVER51'**

(50) Latin Name: *Verbena hybrida*
Varietal Denomination: DANVER51

(76) Inventor: Gabriel Danziger, PO Box 24, Moshav Mishmar Hashiva, Beit Dagan (IL), 50297

( * ) Notice: Subject to any disclaimer, the term of this patent is extended or adjusted under 35 U.S.C. 154(b) by 0 days.

(21) Appl. No.: 12/008,648

(22) Filed: Jan. 11, 2008

(51) Int. Cl.
*A01H 5/00* (2006.01)

(52) U.S. Cl. ..... Plt./308

(58) Field of Classification Search ..... Plt./308
See application file for complete search history.

*Primary Examiner*—Annette H Para

(57) ABSTRACT

A new and distinct *Verbena* cultivar named 'DANVER51' is disclosed, characterized by having clear red flowers, an upright plant habit, highly vigorous growth, and a showing a good tolerance to high temperatures above 35°. The new variety is a *Verbena,* normally produced as an outdoor garden or container plant.

2 Drawing Sheets

Latin name of the genus and species: *Verbena hybrida.*
Variety denomination: 'DANVER51'.

BACKGROUND OF THE INVENTION

The new *Verbena* cultivar is a product of a planned breeding program conducted by the inventor, Gabriel Danziger, in Moshav Mishmar Hashiva, Israel. The objective of the breeding program was to produce new varieties of *Verbena* for commercial introduction. The seed parent is the unpatented, proprietary seedling variety referred to as *Verbena* hybrida 'VE-Z-51.' The pollen parent is unknown as the new variety is the result of an open pollination in which the male parent cannot be identified. The new variety was discovered in June 2006 by the inventor in a group of seedlings resulting from that crossing, in a commercial greenhouse in Moshav Mishmar Hashiva, Israel. Asexual reproduction of the new cultivar 'DANVER51' by vegetative cuttings was first performed at a commercial greenhouse in Moshav Mishmar Hashiva, Israel in October 2006. Subsequent propagation has shown that the unique features of this cultivar are stable and reproduced true to type on successive generations.

SUMMARY OF THE INVENTION

The cultivar 'DANVER51' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DANVER51.' These characteristics in combination distinguish 'DANVER51' as a new and distinct *Verbena* cultivar:

1. Highly vigorous growth habit.
2. Upright plant habit.
3. High temperature tolerance.

Plants of the new cultivar 'DANVER51' are similar to plants of the parent, *Verbena hybrida* 'VE-Z-51' in most horticultural characteristics, however, plants of the new cultivar 'DANVER51' are more vigorous than plants of the seed parent. Additionally, plants of 'DANVER51' have an upright growth habit whereas plants of the seed parent have a trailing growth habit.

COMMERCIAL COMPARISON

Plants of the new cultivar 'DANVER51' are best compared to the commercial variety 'LANAI RED' U.S. patent pending, serial number unknown. Plants of 'DANVER51' are similar to plants of 'LANAI RED' in most horticultural characteristics, however, plants of the new variety produce more incised, narrower foliage, and have a less trailing growth habit.

BRIEF DESCRIPTION OF THE PHOTOGRAPH

Figure 1:
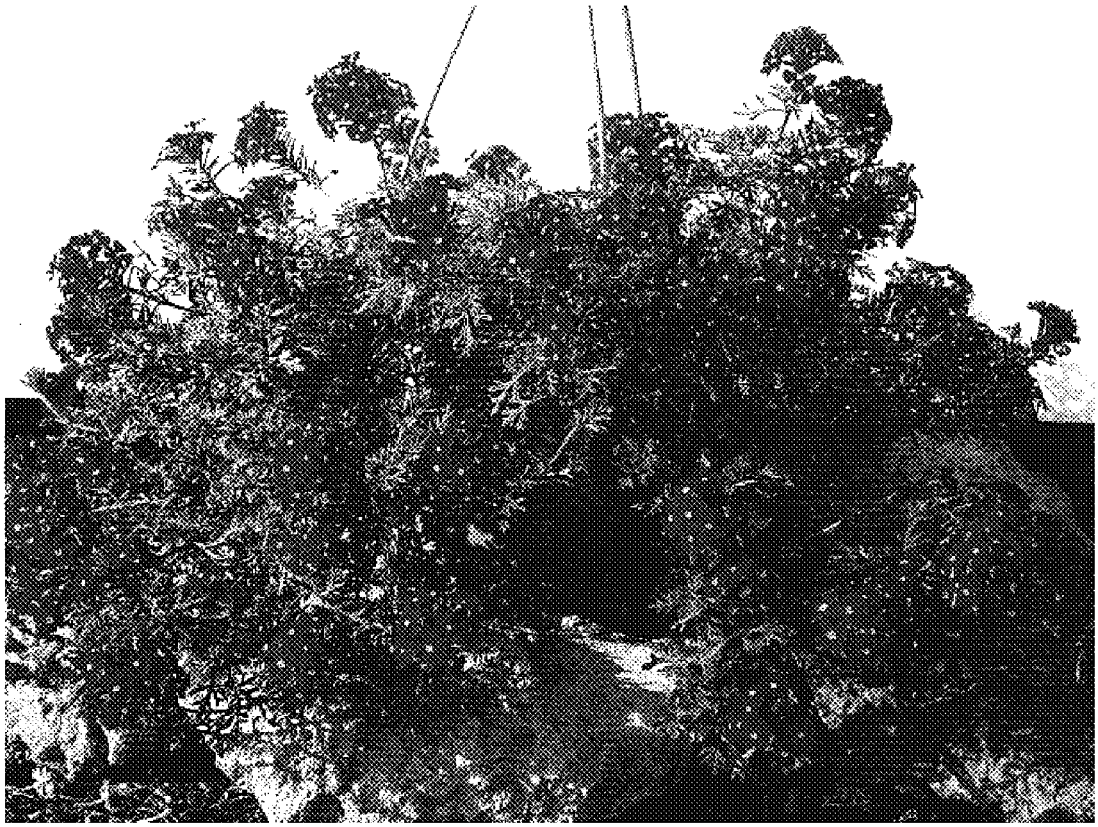

The accompanying photograph in FIG. 1 illustrates in full color a typical plant of 'DANVER51' grown in a greenhouse, in a 16 cm pot. Age of the plant photographed is approximately 10 to 12 weeks days from a rooted cutting, with 3 rooted cuttings planted in the pot.

Figure 2:
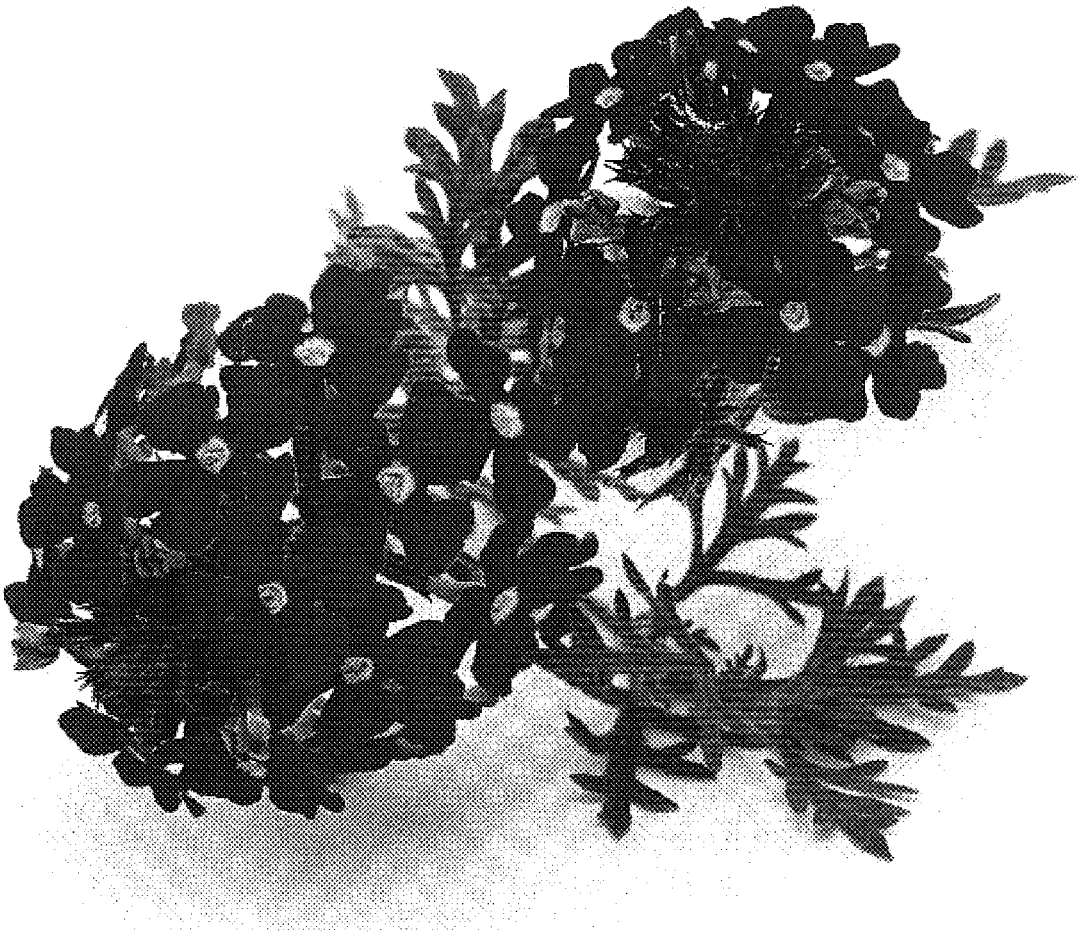

FIG. 2 illustrates in full color a close up of a typical bloom of 'DANVER51'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'DANVER51' plants grown in a greenhouse in Moshav Mishmar Hashiva, Israel. The growing temperature ranged from 20° C. to 28° C. The greenhouse is un-shaded, giving bright, normal sunlight conditions. Measurements and numerical values represent averages of typical plant types.

Botanical classification: *Verbena hybrida* cultivar 'DANVER51.'

PROPAGATION

Time to initiate roots: About 6 days at approximately 18–30° C.
Time to develop roots: About 14 days at approximately 18–30° C.
Root description: Fine, densely fibrous.

PLANT

Growth habit: Spreading.
Pot size of plant described: 12 cm.
Height: Approximately 15 cm.
Plant spread: Approximately 40 cm.
Growth rate: Moderate.
Branching characteristics: Highly branched.
Length of lateral branches: Approximately 30 to 40 cm.
Diameter of lateral branches: Approximately 0.2 cm.
Color of branches: Near RHS Green 143A.
Texture: Pubescent.
Internode length: Approximately 2–3 cm.
Age of plant described: Approximately 60 days from a rooted cutting.

FOLIAGE

Arrangement: Opposite.
Leaves per Branch: Approximately 8–10.
Leaves:
*Size.*—Length: About 2.5 cm. Width: About 2 cm. Shape of leaf: Rhomboidal. Shape of apex: Acute. Shape of base: Acute. Texture: Strigose. Aspect: 45° to stem. Margin type: Incised margin.
*Color.*—Young leaves: Upper surface: RHS Green 137A. Lower surface: RHS Green 137C. Mature leaves: Upper surface: RHS Green 137A. Lower surface: RHS Green 137C.
Petiole: Not Present.
Veins:
*Venation pattern.*—Palmate.
*Color.*—Upper surface: RHS Yellow-Green 149A. Lower surface: RHS Yellow-Green 150A.

FLOWER

Bud: Described 5 days before anthesis.
*Shape.*—Quinquangular.
*Diameter.*—Approximately 0.2 cm.
*Length.*—Approximately 0.8 cm.
*Color.*—Near RHS Green 141C.
Natural flowering season: Summer in Israel.
Flower type: Zygomorphic, salverform.
Corolla:
*Petals/lobes.*—Number: 5. Length: 7 mm. Width: 6 mm. Shape: Oval. Aspect: Upright. Margin: Entire. Texture: Smooth. Color: When opening: Upper surface: Red group 46 B. Lower surface: Red group 53 D. Fully opened: Upper surface: Red groups 145 B. Lower surface: Red group 50B.
*Throat.*—Color: Yellow group 2D. Texture: Slightly pubescent.
*Tube color.*—Green-Yellow group 1C.
Calyx:
*Form.*—Not fused.
*Length.*—1 cm.
*Diameter.*—2 mm.
*Sepal shape.*—Strap-shaped (ligulate).
*Sepal margin.*—Entire.
*Sepal texture.*—Puberulous.
*Sepal color.*—Upper surface: yellow-green 144 B. Lower surface: yellow-green 144 B.
Fragrance: None.
Lasting quality: Individual flower longevity is about 10 days.

REPRODUCTIVE ORGANS

Stamens:
*Number (per flower).*—4.
*Filament length.*—About 0.2 cm.
*Anthers.*—Shape: Oval. Length: About 0.1 cm. Color: RHS Yellow-Green 1B.
Pollen:
*Color.*—RHS Yellow-Green 1C.
*Amount.*—Abundant.
Pistils:
*Quantity per flower.*—1.
*Length.*—About 1 cm.
*Styles.*—Length: About 0.9 cm. Color: Yellow-Green 1D.
*Stigma.*—Shape: Ovoid. Color: Near RHS Yellow-Green 149C.

OTHER CHARACTERISTICS

Disease resistance: Slightly better tolerance of powdery mildew than most commercial varieties.
Temperature tolerance: Good tolerance to low temperature of above 35° C.
Seed and fruit production: Produces small amounts of seed.

What is claimed is:

1. A new and distinct cultivar of *Verbena* plant named 'DANVER51' as herein illustrated and described.

* * * * *